United States Patent
Sugiyama et al.

(10) Patent No.: US 6,303,353 B1
(45) Date of Patent: Oct. 16, 2001

(54) PROCESS FOR PREPARING XYLITOL

(75) Inventors: Masakazu Sugiyama; Shunichi Suzuki; Yasuhiro Mihara; Kenichi Hashiguchi; Kenzo Yokozeki, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/509,547

(22) PCT Filed: Oct. 15, 1998

(86) PCT No.: PCT/JP98/04672

§ 371 Date: Apr. 12, 2000

§ 102(e) Date: Apr. 12, 2000

(87) PCT Pub. No.: WO99/20781

PCT Pub. Date: Apr. 29, 1999

(30) Foreign Application Priority Data

| Oct. 17, 1997 | (JP) | 9-285155 |
| Dec. 1, 1997 | (JP) | 9-330445 |
| Dec. 24, 1997 | (JP) | 9-354674 |
| Jan. 21, 1998 | (JP) | 10-009598 |
| Sep. 11, 1998 | (JP) | 10-258962 |

(51) Int. Cl.⁷ .................................................. C12P 7/18
(52) U.S. Cl. .................. 435/158; 435/157; 435/155; 435/105; 435/72

(58) Field of Search .............................. 435/72, 105, 158, 435/155, 157

(56) References Cited

FOREIGN PATENT DOCUMENTS

| 0-403-392-A2 | 12/1990 | (EP) . |
| 0-421-882-A2 | 4/1991 | (EP) . |
| 47-13707 | * 4/1972 | (JP) . |
| 8-505522 | * 6/1996 | (JP) . |

OTHER PUBLICATIONS

Chemical Abstracts 77:86674 (English Language Abstract of JP 47–13707), 1972.*

Hiroshi Onishi, et al., Microbial Production Xylitol From Glucose, Applied Microbiology, vol. 18, No. 6, Dec. 1969, pp. 1031–1035.

* cited by examiner

Primary Examiner—Francisco Prats
(74) Attorney, Agent, or Firm—Oblon, Spivak, McClelland, Maier & Neustadt, P.C.

(57) ABSTRACT

Xylitol is produced by contacting D-arabitol with a microorganism that belongs to the genus Gluconobacter, Acetobacter, Achromobacter, Agrobacterium, Arthrobacter, Azotobacter, Brevibacterium, Corynebacterium, Erwinia, Flavobacterium, Micrococcus, Nocardia, Planococcus, Pseudomonas, Rhodococcus, Morganella, Actinomadura, Actinomyces, or Streptomyces and is capable of converting D-arabitol to xylitol, and recovering xylitol thus produced.

6 Claims, No Drawings

PROCESS FOR PREPARING XYLITOL

TECHNICAL FIELD

The present invention relates to a method of producing xylitol. Xylitol is useful in the field of food, medicines, and the like.

BACKGROUND ART

The demand for xylitol, which is a sugar alcohol existing in nature, is expected to increase from now on. Xylitol has a lower caloric value than that of sucrose but is sweet as comparable to sucrose. Thus, it is promising as a low caloric sweetener. Furthermore, xylitol is anticariogenic and can be a dental caries-preventing sweetener. Since xylitol does not raise the blood glucose level, it has been used for infusion liquids for treating diabetes.

At present, xylitol is mainly produced in an industrial scale by hydrogenation of D-xylose as described in U.S. Pat. No. 4,008,825. The raw material, D-xylose, can be obtained by hydrolyzing a starting material such as hardwoods, straws, ear stems of corns, crusts of oats, or the other plant-derived materials rich in xylan.

However, D-xylose that is obtained by hydrolyzing the plant materials is disadvantageously expensive because of the high production cost. For example, the yield of the plant material-hydrolyzed product is low, which makes purity of produced D-xylitol low. After the hydrolysis, it is thus necessary to remove the acid used in the hydrolysis and the pigment by the ion exchange treatment. Furthermore, D-xylitol is crystallized to remove other hemicelluloses. Further purification is required to obtain D-xylose that can be used for food. The ion exchange treatment and crystallization results in an increase of the production cost.

In order to solve the above problems, a method of producing xylitol that uses a readily available starting material and that produces a reduced amount of waste matters has been desired. For example, a method of producing xylitol using pentitol as a starting material has been developed. One of the readily available pentitols is D-arabitol that can be produced using yeast (*Can. J. Microbiol.* 31, 1985, 467–471, *J. Gen. Microbiol.* 139, 1993, 1047–1054).

Several methods have been developed for producing xylitol using D-arabitol as a starting material. *Applied Microbiology*, 18, 1969, 1031–1035 reported a method that comprises producing D-arabitol from glucose by fermentation using *Debaryomyces hansenii* ATCC20121, converting D-arabitol thus obtained to D-xylulose using *Acetobacter suboxydans*, and converting D-xylulose to xylitol using *Candida guilliermondii* var. Soya.

EP-A-403392 (applicant: Roquette Freres) and EP-A-421882(applicant: Roquette Freres) each discloses a method which comprises producing D-arabitol by fermentation using an osmotic pressure-resistant yeast, converting D-arabitol thus produced to D-xylulose using a microorganism belonging to the genus Acetobacter, Gluconobacter, or Klebsiella, reacting xylulose thus obtained with glucose (xylose) isomerase to produce a mixture of xylose and xylulose, and converting the thus-formed xylose/xylulose to xylitol by hydrogenation. These publications also disclose a method of preliminarily concentrating xylose in the xylose/xylulose mixture and converting concentrated xylose to xylitol by hydrogenation.

The above-described method of producing xylitol using the D-arabitol above as a starting material enables a high yield production of xylitol. However, it is disadvantageous in requiring plural reaction steps, which makes the process complicated. Thus, the method is not economically satisfactory.

DISCLOSURE OF THE INVENTION

An object of the present invention is to provide a method of producing xylitol using D-arabitol as a starting material and the method achieved by a simple process.

As a result of intensive investigation, the present inventors found microorganisms having the activity to convert D-arabitol to xylitol directly, thereby completing the present invention and solving the above problems.

The present invention relates to a method of producing xylitol comprising the steps of contacting D-arabitol with a microorganism that belongs to the genus Gluconobacter or Acetobacter and is capable of converting D-arabitol to xylitol, and recovering xylitol thus produced.

The present invention also relates to a method of producing xylitol comprising the steps of contacting D-arabitol with a microorganism that belongs to *Gluconobacter suboxydans, Gluconobacter oxydans,* or *Acetobacter xylinum* and is capable of converting D-arabitol to xylitol, and recovering xylitol thus produced.

The present invention further relates to a method of producing xylitol comprising the steps of contacting D-arabitol with a microorganism that belongs to the genus Achromobacter, Agrobacterium, Arthrobacter, Azotobacter, Brevibacterium, Corynebacterium, Erwinia, Flavobacterium, Micrococcus, Nocardia, Planococcus, Pseudomonas, or Rhodococcus and is capable of converting D-arabitol to xylitol, and recovering xylitol thus produced.

Furthermore, the present invention relates to a method of producing xylitol comprising the steps of contacting D-arabitol with a microorganism that belongs to *Achromobacter viscosus, Agrobacterium tumefaciens, Agrobacterium radiobacter, Arthrobacter paraffineus, Arthrobacter hydrocarboglutamicus, Azotobacter indicus, Brevibacterium ketoglutamicum, Corynebacterium fasciens, Erwinia amylovora, Flavobacterium peregrinum, Flavobacterium fucatum,* Micrococcus sp. CCM825, *Nocardia opaca, Planococcus eucinatus, Pseudomonas synxantha,* or *Rhodococcus erythropolis* and is capable of converting D-arabitol to xylitol, and recovering xylitol thus produced.

Moreover, the present invention relates to a method of producing xylitol comprising the steps of contacting D-arabitol with a microorganism that belongs to the genus Morganella, Actinomadura, Actinomyces, or Streptomyces and is capable of converting D-arabitol to xylitol, and recovering xylitol thus produced.

In addition, the present invention relates to a method of producing xylitol comprising the steps of contacting D-arabitol with a microorganism that belongs to *Morganella morganii, Actinomadura madurae, Actinomyces violaceochromogenes, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi,* or *Streptomyces lavendulae* and is capable of converting D-arabitol to xylitol, and recovering xylitol thus produced.

The present invention will be described in detail below.

The microorganisms used in the present invention belong to the genus Gluconobacter, Acetobacter, Achromobacter, Agrobacterium, Arthrobacter, Azotobacter, Brevibacterium, Corynebacterium, Erwinia, Flavobacterium, Micrococcus, Nocardia, Planococcus, Pseudomonas, Rhodococcus, Morganella, Actinomadura, Actinomyces, or Streptomyces and are capable of converting D-arabitol to xylitol.

Examples of the above-described microorganisms include *Gluconobacter suboxydans, Gluconobacter oxydans, Acetobacter xylinum, Achromobacter viscosus, Agrobacterium tumefaciens, Agrobacterium radiobacter, Arthrobacter paraffineus, Arthrobacter hydrocarboglutamicus, Azotobacter indicus, Brevibacterium ketoglutamicum, Corynebacterium fasciens, Erwinia amylovora, Flavobacterium peregrinuim, Flavobacterium fucatum,* Micrococcus sp. CCM825, *Nocardia opaca, Planococcus eucinatus, Pseudomonas synxantha, Rhodococcus erythropolis, Morganella morganii, Actinomadura madurae, Actinomyces violaceochromogenes, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi,* and *Streptomyces lavendulae.*

Specific strains of the microorganisms used in the invention include the following:

*Gluconobacter suboxydans* NRRLB-755;
*Gluconobacter oxydans* ATCC621;
*Gluconobacter oxydans* IAM1842;
*Gluconobacter oxydans* IAM1839;
*Acetobacter xylinum* ATCC14851;
*Achromobacter viscosus* ATCC12448;
*Agrobacterium tumefaciens* ATCC2778;
*Agrobacterium radiobacter* ATCC4718;
*Arthrobacter paraffineus* ATCC15590;
*Arthrobacter paraffineus* ATCC15591;
*Arthrobacter paraffineus* ATCC19064;
*Arthrobacter paraffineus* ATCC19065;
*Arthrobacter hydrocarboglutamicus* ATCC15583;
*Azotobacter indicus* ATCC9037;
*Brevibacterium ketoglutamicum* ATCC15587;
*Brevibacterium ketoglutamicum* ATCC15588;
*Corynebacterium fasciens* IAM1079;
*Erwinia amylovora* IFO12687;
*Flavobacterium peregrinum* CCM1080-A;
*Flavobacterium fucatum* AJ2478;
Micrococcus sp. CCM825;
*Nocardia opaca* NCIB9409;
*Planococcus eucinatus* AJ1656;
*Pseudomonas synxantha* ATCC796;
*Rhodococcus erythropolis* ATCC11048;
*Morganella morganii* AJ2771;
*Actinomadura madurae* ATCC19425;
*Actinomyces violaceochromogenes* IFO13100;
*Streptomyces coelicolor* ATCC10147;
*Streptomyces flavelus* AJ9012;
*Streptomyces griseolus* NRRL B-1062;
*Streptomyces lividans* IFO13385;
*Streptomyces olivaceus* ATCC21379;
*Streptomyces tanashiensis* ATCC15238;
*Streptomyces vilae* AJ9053;
*Streptomyces antibioticus* NRRL3238;
*Streptomyces cacaoi* ATCC19093; and
*Streptomyces lavendulae* ATCC8664.

*Flavobacterium peregrinum* CCM1080-A and Micrococcus sp. CCM825 are available from Czechoslovak Collection of Microorganism, of Tvrdeho 14, Brno CS-602 00, Czechoslovakia.

*Flavobacterium fucatum* AJ2478 was deposited in the Fermentation Research Institute, Agency of Industrial Science and Technology (currently called National Institute of Bioscience and Human-Technology, Agency of Industrial Science and Technology) (address: 1-3, Higashi 1-chome, Tsukuba-shi, Ibaraki 305–8566, Japan) on Apr. 25, 1983 under the accession number FERM P-7053 and transferred to the international deposition in accordance with the Budapest Treaty on Sep. 9, 1998 under the accession number FERM BP-6492.

*Planococcus eucinatus* AJ1656 was deposited with the Fermentation Research Institute, Agency of Industrial Science and Technology (currently called National Institute of Bioscience and Human-Technology, Agency of Industrial Science and Technology) on Jan. 19, 1987 under the accession number FERM P-9133 and transferred to the international deposition in accordance with the Budapest Treaty on Sep. 9, 1998 under the accession number FERM BP-6493.

*Morganella morganii* AJ2771 was deposited with the Fermentation Research Institute, Agency of Industrial Science and Technology (currently called National Institute of Bioscience and Human-Technology, Agency of Industrial Science and Technology) on Jan. 16, 1998 under the accession number FERM P-16594 and transferred to the international deposition in accordance with the Budapest Treaty on Sep. 9, 1998 under the accession number FERM BP-6496.

*Streptomyces flavelus* AJ9012 was deposited with the Fermentation Research Institute, Agency of Industrial Science and Technology (currently called National Institute of Bioscience and Human-Technology, Agency of Industrial Science and Technology) on Jan. 16, 1998 under the accession number FERM P-16585 and transferred to the international deposition in accordance with the Budapest Treaty on Sep. 9, 1998 under the accession number FERM BP-6494.

*Streptomyces virginiae* AJ9053 was deposited with the Fermentation Research Institute, Agency of Industrial Science and Technology (currently called National Institute of Bioscience and Human-Technology, Agency of Industrial Science and Technology) on Jan. 16, 1998 under the accession number FERM P-16587 and transferred to the international deposition in accordance with the Budapest Treaty on Sep. 9, 1998 under the accession number FERM BP-6495.

*Nocardia opaca* NCIB9409 is available from National Collections of Industrial and Marine Bacteria, of NCIMB Lts., Torry Research Station, 135 Abbey Road, Aberdeen AB9 8DG, United Kingdom.

*Erwinia amylovora* IFO12687, *Actinomyces violaceochromogenes* IFO13100, and *Streptomyces lividans* IFO13385 are available from Institute for Fermentation, Osaka, of 17-85, Juso-honmachi 2-chome, Yodogawa-ku, Osaka 532, Japan.

*Corynebacterium fasciens* IAM1079, *Gluconobacter oxydans* IAM 1842, and *Gluconobacter oxydans* IAM 1839 are available from Institute of Molecular and Cellular Biosciences (formerly Institute of Applied Microbiology), of The University of Tokyo, Yayoi 1-chome, Bunkyo-ku, Tokyo, Japan).

Media for culturing these microorganisms are not particularly limited and usual media containing usually used carbon sources, nitrogen sources, inorganic ions, and, if necessary, organic nutrients, can be used. As the carbon sources, carbohydrates such as glucose, alcohols such as glycerol, organic acids, or the like can be appropriately used. The nitrogen sources include ammonia gas, aqueous ammonia, ammonium salts, nitrates, or the like. The phosphorus sources include potassium phosphate, sodium phosphate, or the like. As the inorganic ions, magnesium ions, potassium ions, iron ions, manganese ions, sulfate ions, or the like can be appropriately used if required. Suitable organic nutrients include vitamins, amino acids, and liver extract, yeast extract, malt extract, peptone, meat extract, corn steep liquor, casein hydrolyzing products, or the like containing vitamins and amino acids.

The activity of converting D-arabitol to xylitol can sometimes be increased by adding to the medium inducers of enzymes that catalyze the reaction to produce xylitol from D-arabitol such as carbohydrates or sugar alcohols including D-xylose, D-xylulose, D-arabitol, xylitol, or the like.

The culturing conditions are also not particularly limited. For example, culturing may be carried out for 12 to 72 hours with controlling the pH value within pH 5 to 8 and the temperature within the 25 to 40° C. under aerobic conditions.

The microorganisms cultured as described above are contacted with D-arabitol to produce xylitol in the reaction mixture. In the method of the present invention, the above-described "microorganism" may be microbial cells themselves or preparation products of the microbial cells as long as the products are capable of converting D-arabitol to xylitol. Specifically, such preparation products include the culture containing the microbial cells, microbial cells that are separated and recovered from the culture, immobilized products of the microbial cells, the microbial cells treated with acetone, or freeze-dried, cell disrupted solution, fractions or purified enzyme fractions of the cell disrupted solution, and immobilized products of these treated cells.

A good result can be obtained by performing the reaction at 20 to 60° C., preferably 30 to 40° C., at pH 4.0 to 9.0, preferably 6.5 to 7.5. The yield of xylitol can sometimes be increased by preventing reduction of the pH value during the reaction by, for example, adding calcium carbonate to the reaction mixture to give a concentration of 2% (w/v). Both of stationary reaction and stirring reaction can be used. The reaction period is preferably from 1 to 100 hours though it varies depending on the conditions such as the activity of the microorganism used or the concentration of D-arabitol.

There is a case that the yield of xylitol is increased when a carbon source is added upon the reaction. Particularly, a carbon source is preferably added when the bacteria belonging to Acetobacter or Gluconobacter is used. Examples of the carbon sources to be added include carbohydrates, carbohydrate derivatives, alcohols, aldehydes, and organic acids. The carbohydrates include glucose, fructose, sucrose, and lactose. The carbohydrate derivatives include sugar alcohols such as sorbitol, mannitol, or glycerol, aldonic acids such as gluconic acid. The alcohols include methanol, ethanol, propanol, isopropyl alcohol, 1,4-butanediol, and 2,3-butanediol. The aldehydes include formaldehyde, acetoaldehyde, propionaldehyde, isobutylaldehyde, and glyceraldehyde. The organic acids include formic acid, citric acid, fumaric acid, and malic acid. These carbon sources may be used alone or as a mixture of two or three or more thereof. The amount of the carbon sources varies depending on the activity of the microorganism used, the concentration of D-arabitol and the like conditions. A good result can be obtained when the carbon sources is used in a total amount of 0.5 to 30% (w/v), preferably 0.5 to 10% (w/v).

When a preparation product of the microbial cells such as a solution of the disrupted microbial cells is used as a microorganism, the reduction reaction of D-xylulose can efficiently proceed by directly adding NAD or NADH to the reaction system. In this occasion, NADH is added when bacteria belonging to the genus Gluconobacter or Acetobacter are used as microorganisms, while NAD is preferably added when bacteria belonging to the genus Achromobacter, Agrobacterium, Arthrobacter, Azotobacter, Brevibacterium, Corynebacterium, Erwinia, Flavobacterium, Micrococcus, Nocardia, Planococcus, Pseudomonas, Rhodococcus, Morganella, Actinomadura, Actinomyces, or Streptomyces are used.

Xylitol produced in the culture medium as described above is recovered and isolated from the reaction mixture by the conventional methods. Specifically, the solid matter is removed by centrifugation, filtration, or the like method, the resulting liquid fraction is decolored and desalted using activated carbon or an ion-exchange resin, and the desired product is crystallized from the solution.

BEST MODE FOR CARRYING OUT THE INVENTION

The present invention will be illustrated in more detail with reference to examples, but is not to be construed to be limited to the examples. In the following examples, the starting material, D-arabitol, and xylitol produced were analyzed by high performance liquid chromatography (HPLC) under the following conditions:

Column: Shodex SC1211 (product of Showa Denko)

Mobile phase: 50% acetonitrile/50% 50 ppm Ca-EDTA aqueous solution

Flow rate: 0.8 ml/min

Temperature: 60° C.

Detection: RI detector

EXAMPLE 1

Four ml of a medium (pH 7.0) containing 1.8% (w/v) of normal bouillon (product of Eiken Chemical) was distributed into a test tube and sterilized by heating at 120° C. for 20 minutes. Separately sterilized D-arabitol, xylitol and D-xylose were each added to the medium to give a concentration of 1%. The resulting medium was inoculated with the respective microorganisms shown in Table 1 and incubated at 30° C. for 2 days with shaking. The microbial cells are harvested from the culture medium by centrifugation and washed once with physiological saline.

Each of the cultured microbial cells were suspended in 0.1 M phosphate buffer (pH 7.0) to give a concentration of 5% (w/v) in terms of the wet weight. Glass beads (Biospec products, diameter: 0.1 mm) were added to the microbial cells suspension in about a half amount of the suspension. The microbial cells were then disrupted with a multibeads shocker MB-200 (Yasui Kikai). The disruption was performed at 3000 rpm for 3 minutes and the thus-obtained microbial cell suspension was subjected to the following conversion reaction as a crude enzyme solution.

D-arabitol and NAD were dissolved in 0.1 M Tris-hydrochloric acid buffer (pH 8.0) to a final concentration of 5% (w/v) and 10 mM, respectively. The. resulting solution was distributed into test tubes in 0.9 ml portions each. Each of the crude enzyme solution (0.1 ml) was added to this reaction mixture and allowed to react at pH 8.0 at 30° C. for 22 hours. After completion of the reaction, the precipitate thus formed was removed by centrifugation and xylitol formed was determined by HPLC. The results are shown in Table 1. As shown in Table 1, xylitol was efficiently produced and accumulated from D-arabitol in the reaction using any of the microorganisms used.

TABLE 1

Concentration and yield of xylitol produced by the reaction

| Strain | Xylitol produced (g/l) | Yield (%) |
|---|---|---|
| Achromobacter viscosus ATCC12448 | 0.1 | 0.2 |
| Agrobacterium tumefaciens ATCC2778 | 0.3 | 0.6 |
| Agrobacterium radiobacter ATCC4718 | 0.6 | 1.2 |
| Arthrobacter paraffineus ATCC15590 | 2.6 | 5.2 |
| Arthrobacter paraffineus ATCC15591 | 4.4 | 8.8 |
| Arthrobacter paraffineus ATCC19064 | 3.7 | 7.4 |
| Arthrobacter paraffineus ATCC19065 | 3.6 | 7.2 |
| Arthrobacter hydrocarboglutamicus ATCC15583 | 4.0 | 8.0 |
| Azotobacter indicus ATCC9037 | 0.3 | 0.6 |
| Brevibacterium ketoglutamicum ATCC15587 | 2.2 | 4.4 |
| Brevibacterium ketoglutamicum ATCC15588 | 3.4 | 6.8 |
| Corynebacterium fasciens IAM1079 | 1.6 | 3.2 |
| Erwinia amylovora IFO12687 | 4.3 | 8.6 |
| Flavobacterium peregrinum CCM1080-A | 0.3 | 0.6 |
| Flavobacterium fucatum FERM P-7053 | 1.2 | 2.4 |
| Micrococcus sp. CCM825 | 0.2 | 0.4 |
| Nocardia opaca NCIB9409 | 3.8 | 7.6 |
| Planococcus eucinatus FERM P-9133 | 0.5 | 1.0 |
| Pseudomonas synxantha ATCC796 | 0.2 | 0.4 |
| Rhodococcus erythropolis ATCC11048 | 5.5 | 11.0 |
| Morganella morganii AJ2771 | 1.7 | 3.4 |

EXAMPLE 2

Fifty ml of a medium (pH 7.2) containing 0.2% (w/v) yeast extract, 0.2% meat extract, 0.4% peptone, 0.5% NaCl and 0.2% magnesium sulfate heptahydrate was put into a 500-ml flask and sterilized by heating at 120° C. for 20 minutes. Separately, sterilized D-arabitol, xylitol and D-xylose were each added to the resulting medium to give a respective concentration of 1%. Each of the medium was inoculated with the respective microorganisms listed in Table 2 and cultured at 30° C. for 2 days with shaking. The microbial cells were collected by centrifugation from the culture medium and washed once with physiological saline.

The respective cultured microbial cells were suspended in 0.1M phosphate buffer (pH 7.0) to give a concentration of 5% (w/v) in terms of wet weight. Glass beads (Biospec products, diameter of 0.1 mm) were added to the microbial cell suspensions in about a half amount of the suspension and the microbial cells were disrupted with a multibeads shocker MB-200 (Yasui Kikai) at 3000 rpm for 3 minutes. The resulting microbial cell suspension was subjected to the following conversion reaction as a crude enzyme solution.

D-arabitol and NAD were dissolved in 0.1M Tris-hydrochloride buffer (pH 8.0) to give a final concentration of 5% (w/v) and 10 mM, respectively. A 0.9 ml portion of the resulting mixture was distributed into test tubes. Each of the crude enzyme solution (0.1 ml) was added to the resulting reaction mixture and allowed to react at pH 8.0 and 30° C. for 22 hours. After completion of the reaction, the precipitates were removed by centrifugation and xylitol thus formed was determined by HPLC. The results are shown in Table 2. As shown in Table 2, xylitol was efficiently produced and accumulated from D-arabitol by the reaction using any of the microorganisms.

TABLE 2

Concentration and yield of xylitol produced by the reaction

| Strain | Xylitol produced (g/l) | Yield (%) |
|---|---|---|
| Actinomadura madurae ATCC19425 | 0.5 | 1.0 |
| Actinomyces violaceochromogenes IFO13100 | 0.1 | 0.2 |
| Streptomyces coelicolor ATCC10147 | 0.5 | 1.0 |
| Streptomyces flavelus AJ9012 | 0.3 | 0.6 |
| Streptomyces griseolus NRRL B-1062 | 0.4 | 0.8 |
| Streptomyces lividans IFO13385 | 0.4 | 0.8 |
| Streptomyces olivaceus ATCC21379 | 0.3 | 0.6 |
| Streptomyces tanashiensis ATCC15238 | 0.9 | 1.8 |
| Streptomyces virginiae AJ9053 | 0.5 | 1.0 |
| Streptomyces antibioticus NRRL3238 | 0.1 | 0.2 |
| Streptomyces cacaoi ATCC19093 | 0.1 | 0.2 |
| Streptomyces lavendulae ATCC8664 | 0.1 | 0.2 |

EXAMPLE 3

Fifty ml of a medium (pH 7.0) containing 2.4% (w/v) potato dextrose (Difco), 3% yeast extract (Difco), 2.5% Bacto liver infusion (Difco), 0.5% meat extract (Difco) and 1.5% glycerol was distributed in 500-ml Sakaguchi (shouldered) flasks and sterilized by heating at 120° C. for 20 minutes. Separately, sterilized D-arabitol, xylitol and D-xylose were each added to the resulting medium to give a concentration of 0.5% and calcium carbonate was added thereto to give a concentration of 2.5%. Each of these media was inoculated with Gluconobacter oxydans ATCC621, Gluconobacter suboxydans NRRLB-755, or Acetobacter xylinum ATCC14851 and cultivated at 30° C. for 3 days with shaking. The microbial cells were harvested from the culture medium by centrifugation and washed once with physiological saline.

D-arabitol and D-glucose were dissolved in 0.1 M phosphate buffer (pH 7.5) to give a concentration of 5% (w/v) and 1%, respectively. The resulting mixture was distributed into test tubes in a 10-ml portion, inoculated with each of the cultured microbial cells in an amount of about 5% (w/v) in terms of the wet weight, and cultured at pH 7.5 and 30° C. for 22 hours with shaking.

After completion of the reaction, the microbial cells were removed by centrifugation and xylitol thus produced was determined by HPLC. The results are shown in Table 3. As shown in Table 3, xylitol was efficiently produced and accumulated from D-arabitol by the reaction using any of the microorganisms.

TABLE 3

Concentration and yield or xylitol produced by the reaction

| Strain | Concentration of xylitol produced (g/l) | Yield (%) |
|---|---|---|
| Gluconobacter suboxydans NRRL B-755 | 5.8 | 12 |
| Gluconobacter oxydans ATCC621 | 17 | 33 |
| Acetobacter xylinum ATCC14851 | 11 | 22 |

EXAMPLE 4

Forty ml of a medium (pH 7.0) containing 2.4% (w/v) potato dextrose (Difco), 3% yeast extract (Difco), 0.5% meat extract (Difco) and 1.5% glycerol was distributed in 500-ml Sakaguchi (shouldered) flasks and sterilized by heating at 120° C. for 15 minutes. Separately, sterilized D-arabitol, xylitol and D-xylose were each added to the resulting mixture to 1.0% and calcium carbonate were added thereto to 2.0%. This medium was inoculated with *Gluconobacter oxydans* ATCC621 and cultured at 30° C. for 3 days with shaking. The microbial cells were harvested from the culture medium by centrifugation and washed once with physiological saline.

D-arabitol and D-glucose were dissolved in 0.1 M phosphate buffer (pH 6.0) to 5% (w/v) and 1%, respectively. The resulting mixture was distributed into test tubes in 10-ml portions each, and inoculated with the microbial cell in an amount of 10% (w/v) by a wet weight. In addition, calcium carbonate was added thereto to 2% (w/v). The resulting medium was cultured at 30° C. with shaking. For comparison, ethanol or glucose was added to the culture medium six hours after the commencement of culturing in such a manner as shown in Table 4. After 27 hours, the microbial cells were removed by centrifugation and xylitol thus produced was determined by HPLC. The results are shown in Table 4. As shown in Table 4, the amount of xylitol produced from D-arabitol was increased by addition of the carbon source.

TABLE 4

Concentration and yield of xylitol produce by the reaction (Strain used: *Gluconobacter oxydans* ATCC621)

| Compound added 6 hours after the commencement of the reaction | Concentration of xylitol produced (g/l) | Yield (%) |
|---|---|---|
| None | 28 | 56 |
| Ethanol 5% | 34 | 70 |
| Glucose 0.5% | 29 | 58 |
| Ethanol 5% and glucose 0.5% | 47 | 94 |

EXAMPLE 5

Forty ml of a medium (pH 7.0) containing 2.4% (w/v) potato dextrose (Difco), 3% yeast extract (Difco), 0.5% meat extract (Difco) and 1.5% glycerol (pH 7.0) was distributed in 500-ml Sakaguchi (shouldered) flasks and sterilized by heating at 120° C. for 15 minutes. Separately sterilized D-arabitol, xylitol and D-xylose were added to the resulting medium to 1.0% and calcium carbonate were added thereto to 2.0%, respectively. This medium was inoculated with *Gluconobacter suboxydans* NRRLB-755 or *Acetobacter xylinum* ATCC14851 and cultivated at 30° C. for 3 days with shaking. The microbial cells were harvested from the culture medium by centrifugation and washed once with physiological saline.

D-arabitol and D-glucose were dissolved in 0.1 M phosphate buffer (pH 6.0) to give a concentration of 5% (w/v) and 1%, respectively. The resulting mixture was distributed into test tubes in 10-ml portions each, and inoculated with the microbial cell in an amount of about 10% (w/v) in terms of a wet weight. In addition, calcium carbonate was added thereto to a concentration of 2% (w/v). The resulting medium was cultured at 30° C. with shaking. For comparison, 5% ethanol and 0.5% glucose were added to the culture medium six hours after the commencement of culturing. After 27 hours, the microbial cells were removed by centrifugation and xylitol thus produced was determined by HPLC. The results are shown in Table 5. As shown in Table 5, xylitol was efficiently produced and accumulated from D-arabitol.

TABLE 5

Concentration and yield of xylitol produced by the reaction

| Strain | Concentration of xylitol produced (g/l) | Yield (%) |
|---|---|---|
| *Gluconobacter suboxydans* NRRL B-755 | 16 | 32 |
| *Acetobacter xylinum* ATCC14851 | 32 | 64 |

EXAMPLE 6

Fifty ml of a medium (pH 7.0) containing 2.4% (w/v) potato dextrose (Difco), 3% yeast extract (Difco), 0.5% meat extract (Difco) and 1.5% glycerol was distributed in 500-ml Sakaguchi (shouldered) flasks and sterilized by heating at 120° C. for 15 minutes. A D-arabitol solution was sterilized at 120° C. for 15 minutes and added to the above-described medium to 3.0%. Furthermore, 1 g of calcium carbonate was sterilized at 200° C. for 120 minutes and added to the above medium. This medium was inoculated with *Gluconobacter oxydans* ATCC621 and cultivated at 30° C. for 3 days with shaking. The microbial cells were harvested from the culture medium by centrifugation and washed once with physiological saline.

D-arabitol was dissolved in 0.1 M phosphate buffer (pH 6.0) to a concentration of 5% (w/v). The washed microbial cells as obtained above was added thereto to about 10% (w/v) in terms of the wet weight. A 10-ml portion of the thus-obtained reaction mixture was added to a test tube and allowed to react at 30° C. with shaking. After 24 hours, the microbial cells were removed by centrifugation and xylitol thus produced was determined by HPLC. The results are shown in Table 6. As shown in Table 6, xylitol was produced and accumulated from D-arabitol.

TABLE 6

Concentration and yield of xylitol produce by the reaction

| Strain | Concentration of Xylitol produced (g/l) | Yield (%) |
|---|---|---|
| *Gluconobacter oxydans* ATCC621 | 7.8 | 16 |

Industrial Applicability

The present invention enables producing xylitol by a simple process using D-arabitol as a starting material.

What is claimed is:

1. A method of producing xylitol, comprising the steps of:
   contacting D-arabitol with a microorganism which belongs to the genus Gluconobacter or Acetobacter and is capable of converting D-arabitol to xylitol, and recovering xylitol thus produced.

2. The method of claim 1, wherein the microorganism belonging to the genus Gluconobacter or Acetobacter is *Gluconobacter suboxydans, Gluconobacter oxydans*, or *Acetobacter xylinum*.

3. A method of producing xylitol, comprising the steps of:

contacting D-arabitol with a microorganism which belongs to the genus Achromobacter, Agrobacterium, Arthrobacter, Azotobacter, Brevibacterium, Corynebacterium, Erwinia, Flavobacterium, Micrococcus, Nocardia, Planococcus, Pseudomonas, or Rhodococcus and is capable of converting D-arabitol to xylitol, and recovering xylitol thus produced.

4. The method of claim 3, wherein the microorganism belonging to the genus Achromobacter is *Achromobacter viscosus*, the microorganism belonging to the genus Agrobacterium is *Agrobacterium tumefaciens* or *Agrobacterium radiobacter*, the microorganism belonging to the genus Arthrobacter is *Arthrobacter paraffineus* or *Arthrobacter hydrocarboglutamicus*, the microorganism belonging to the genus Azotobacter is *Azotobacter indicus*, the microorganism belonging to the genus Brevibacterium is *Brevibacterium ketoglutamicum*, the microorganism belonging to the genus Corynebacterium is *Corynebacterium fasciens*, the microorganism belonging to the genus Erwinia is *Erwinia amylovora*, the microorganism belonging to the genus Flavobacterium is *Flavobacterium peregrinum* or *Flavobacterium fucatum*, the microorganism belonging to the genus Micrococcus is Micrococcus sp. CCM825, the microorganism belonging to the genus Nocardia is *Nocardia opaca*, the microorganism belonging to the genus Planococcus is *Planococcus eucinatus*, the microorganism belonging to the genus Pseudomonas is *Pseudomonas synxantha*, and the microorganism belonging to the genus Rhodococcus is *Rhodococcus erythropolis*.

5. A method of producing xylitol, comprising the steps of:

contacting D-arabitol with a microorganism that belongs to the genus Morganella, Actinomadura, Actinomyces, or Streptomyces and is capable of converting D-arabitol to xylitol, and recovering xylitol thus produced.

6. The method of claim 5, wherein the microorganism belonging to the genus Morganella is *Morganella morganii*, the microorganism belonging to the genus Actinomadura is *Actinomadura madurae*, the microorganism belonging to the genus Actinomyces is *Actinomyces violaceochromogenes*, and the microorganism belonging to the genus Streptomyces is *Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi,* or *Streptomyces lavendulae*.

\* \* \* \* \*

UNITED STATES PATENT AND TRADEMARK OFFICE
CERTIFICATE OF CORRECTION

PATENT NO. : 6,303,353 B1  Page 1 of 1
DATED : October 16, 2001
INVENTOR(S) : Masakazu Sugiyama et al.

It is certified that error appears in the above-identified patent and that said Letters Patent is hereby corrected as shown below:

<u>Title page, Item [54] and Column 1, line 1,</u>
The Title should read:

-- [54] METHOD OF PRODUCING XYLITOL --

Signed and Sealed this

Thirteenth Day of August, 2002

Attest:

Attesting Officer

JAMES E. ROGAN
*Director of the United States Patent and Trademark Office*